(12) United States Patent
Thomas (10) Patent No.: US 7,286,941 B1
(45) Date of Patent: Oct. 23, 2007

(54) METHOD FOR HAPLOTYPE ANALYSIS

(75) Inventor: Alun Thomas, Salt Lake City, UT (US)

(73) Assignee: Myriad Genetics, Inc., Salt Lake City, UT (US)

(*) Notice: Subject to any disclaimer, the term of this patent is extended or adjusted under 35 U.S.C. 154(b) by 467 days.

(21) Appl. No.: 10/639,237

(22) Filed: Aug. 11, 2003

Related U.S. Application Data (60) Provisional application No. 60/402,439, filed on Aug. 9, 2002.

(51) Int. Cl.
*G06F 19/00* (2006.01)

(52) U.S. Cl. ..................................................... 702/19

(58) Field of Classification Search ..................... None
See application file for complete search history.

(56) References Cited

U.S. PATENT DOCUMENTS 6,291,182 B1  9/2001  Schork et al.

FOREIGN PATENT DOCUMENTS

WO     WO 02/101631     12/2002

OTHER PUBLICATIONS

Ceppellini, R. et al., "The Estimation of Gene Frequencies in a Random-Mating Population", *Annals Hum. Gen.*, 1955; 20(2):97-115.

Dempster, A.P., et al., "Maximum Likelihood from Incomplete Data via the *EM* Algorithm", *J. Roy. Stat. Soc., Ser. B*, 1977; 39:1-38.

Clark, Andrew G., "Inference of Haplotypes from PCR-amplified Samples of Diploid Populations", *Mol. Biol. Evol.*, 1990; 7(2):111-122.

Excoffier, Laurent, et al., "Maximum-Likelihood Estimation of Molecular Haplotype Frequencies in a Diploid Population", *Mol. Biol. Evol.*, 1995; 12(5):921-927.

Hawley, et al., "HAPLO: a program using the EM algorithm to estimate the frequencies of multi-site haplotypes", *J. Hered.*, 1995; 86(5):409-411.

Long, Jeffrey C., et al., "An E-M Algorithm and Testing Strategy for Multiple-Locus Haplotypes", *Am. J. Hum. Genet.*, 1995; 56:799-810.

Stephens, Matthew, et al., "A New Statistical Method for Haplotype Reconstruction from Population Data", *Am. J. Hum. Genet.*, 2001; 68:978-989.

Niu, Tianhua, et al., "Bayesian Haplotype Inference for Multiple Linked Single-Nucleotide Polymorphisms", *Am. J. Hum. Genet.*, 2002; 70:157-169.

Qin, Zhaohui S., et al., "Partition-Ligation-Expectation-Maximization Algorithm for Haplotype Inference with Single-Nucleotide Polymorphisms", *Am. J. Hum. Genet.*, 2002; 71:1242-1247.

*Primary Examiner*—Lori A. Clow
(74) *Attorney, Agent, or Firm*—Jonathan A. Baker; Jay Z. Zhang; Myriad I.P. Department (57) ABSTRACT

The invention relates to a method for determining haplotypes. The method is capable of providing phase information from a set of unphased genotype observations in an efficient robust manner. The method is capable of handling large datasets that include missing data.

9 Claims, 4 Drawing Sheets

Figure 1

| Set of Loci or Markers | 1 | 2 | 3 | 4 | 5 | 6 | 7 | 8 | 9 | 10 | 11 |
|---|---|---|---|---|---|---|---|---|---|---|---|
|  | * | * | * | * | * | * | * | * | * | * | * |
| Select, combine, analyze | * | * |  |  |  |  |  |  |  |  |  |
| Select, combine, analyze | * | * | * |  |  |  |  |  |  |  |  |
| Select, combine, analyze |  |  |  |  |  |  |  |  |  | * | * |
| Select, combine, analyze | * | * | * | * |  |  |  |  |  |  |  |
| Select, combine, analyze |  |  |  |  |  |  | * | * |  |  |  |
| Select, combine, analyze |  |  |  |  |  |  | * | * | * | * | * |
| Select, combine, analyze |  |  |  |  | * | * |  |  |  |  |  |
| Select, combine, analyze | * | * | * | * | * | * |  |  |  |  |  |
| Select, combine, analyze | * | * | * | * | * | * | * | * | * | * | * |
|  |  |  |  |  |  |  |  |  |  |  |  |

FIGURE 2

| Set of Loci or Markers | 1 | 2 | 3 | 4 | 5 | 6 | 7 | 8 | 9 | 10 | 11 |
|---|---|---|---|---|---|---|---|---|---|---|---|
| | * | * | * | * | * | * | * | * | * | * | * |
| Select, combine, analyze | * | * | | | | | | | | | |
| Select, combine, analyze | * | * | * | | | | | | | | |
| Select, combine, analyze | * | * | * | * | | | | | | | |
| Select, combine, analyze | * | * | * | * | * | | | | | | |
| Select, combine, analyze | * | * | * | * | * | * | | | | | |
| Select, combine, analyze | * | * | * | * | * | * | * | | | | |
| Select, combine, analyze | * | * | * | * | * | * | * | * | | | |
| Select, combine, analyze | * | * | * | * | * | * | * | * | * | | |
| Select, combine, analyze | * | * | * | * | * | * | * | * | * | * | |
| Select, combine, analyze | * | * | * | * | * | * | * | * | * | * | * |

SEQUENCE LISTING

```
<160> NUMBER OF SEQ ID NOS: 28

<210> SEQ ID NO 1
<211> LENGTH: 10
<212> TYPE: DNA
<213> ORGANISM: Artificial Sequence
<220> FEATURE:
<223> OTHER INFORMATION: Chemically Synthesized

<400> SEQUENCE: 1
atttggccta                                                          10

<210> SEQ ID NO 2
<211> LENGTH: 10
<212> TYPE: DNA
<213> ORGANISM: Artificial Sequence
<220> FEATURE:
<223> OTHER INFORMATION: Chemically Synthesized

<400> SEQUENCE: 2
atctgggctt                                                          10

<210> SEQ ID NO 3
<211> LENGTH: 26
<212> TYPE: DNA
<213> ORGANISM: Homo sapiens

<400> SEQUENCE: 3
ccaggctgat aatatccagt aaggca                                        26

<210> SEQ ID NO 4
<211> LENGTH: 26
<212> TYPE: DNA
<213> ORGANISM: Homo sapiens

<400> SEQUENCE: 4
```

```
ccaagctgat aatatccagt aaggca                                          26
```

<210> SEQ ID NO 5
<211> LENGTH: 26
<212> TYPE: DNA
<213> ORGANISM: Homo sapiens

<400> SEQUENCE: 5

```
ccagactgat aatatccagt aaggca                                          26
```

<210> SEQ ID NO 6
<211> LENGTH: 26
<212> TYPE: DNA
<213> ORGANISM: Homo sapiens

<400> SEQUENCE: 6

```
ccaggctgat aatatccagt aaggcg                                          26
```

<210> SEQ ID NO 7
<211> LENGTH: 26
<212> TYPE: DNA
<213> ORGANISM: Homo sapiens

<400> SEQUENCE: 7

```
ctcggctgat aatatccagt aaggca                                          26
```

<210> SEQ ID NO 8
<211> LENGTH: 26
<212> TYPE: DNA
<213> ORGANISM: Homo sapiens

<400> SEQUENCE: 8

```
ctcagctgat aatatccagt aagtca                                          26
```

<210> SEQ ID NO 9
<211> LENGTH: 26
<212> TYPE: DNA
<213> ORGANISM: Homo sapiens

<400> SEQUENCE: 9

```
ctcagctgat aatatccagt aaagca                                          26
```

<210> SEQ ID NO 10
<211> LENGTH: 26
<212> TYPE: DNA
<213> ORGANISM: Homo sapiens

<400> SEQUENCE: 10

```
ctcggctgat aatatccagt aaagca                                          26
```

<210> SEQ ID NO 11
<211> LENGTH: 26
<212> TYPE: DNA
<213> ORGANISM: Homo sapiens

<400> SEQUENCE: 11

```
ctcgactgat aatatccagt aaggca                                          26
```

<210> SEQ ID NO 12
<211> LENGTH: 26
<212> TYPE: DNA
<213> ORGANISM: Homo sapiens -continued

```
<400> SEQUENCE: 12
ctcggctgat aatacccagt aaggcg                                          26

<210> SEQ ID NO 13
<211> LENGTH: 26
<212> TYPE: DNA
<213> ORGANISM: Homo sapiens

<400> SEQUENCE: 13
ctcagctgat aatatccagt aaggcg                                          26

<210> SEQ ID NO 14
<211> LENGTH: 26
<212> TYPE: DNA
<213> ORGANISM: Homo sapiens

<400> SEQUENCE: 14
ctcagctgat aatatccagt aaatcg                                          26

<210> SEQ ID NO 15
<211> LENGTH: 26
<212> TYPE: DNA
<213> ORGANISM: Homo sapiens

<400> SEQUENCE: 15
ctcagctgat aatatccagg aaggcg                                          26

<210> SEQ ID NO 16
<211> LENGTH: 26
<212> TYPE: DNA
<213> ORGANISM: Homo sapiens

<400> SEQUENCE: 16
ctcagctgac aatatccagt aaggca                                          26

<210> SEQ ID NO 17
<211> LENGTH: 26
<212> TYPE: DNA
<213> ORGANISM: Homo sapiens

<400> SEQUENCE: 17
ctcaactgat aatatccagt agggca                                          26

<210> SEQ ID NO 18
<211> LENGTH: 26
<212> TYPE: DNA
<213> ORGANISM: Homo sapiens

<400> SEQUENCE: 18
ccaggttgat aatatccagt aaggcg                                          26

<210> SEQ ID NO 19
<211> LENGTH: 26
<212> TYPE: DNA
<213> ORGANISM: Homo sapiens

<400> SEQUENCE: 19
ccaggctgat gatatccagt aaggcg                                          26

<210> SEQ ID NO 20
<211> LENGTH: 26
<212> TYPE: DNA
<213> ORGANISM: Homo sapiens
```

```
<400> SEQUENCE: 20
ccaggctgat aatatctagt aaggca                                              26

<210> SEQ ID NO 21
<211> LENGTH: 26
<212> TYPE: DNA
<213> ORGANISM: Homo sapiens

<400> SEQUENCE: 21
ccaggctgat aatatccaat aaggcg                                              26

<210> SEQ ID NO 22
<211> LENGTH: 26
<212> TYPE: DNA
<213> ORGANISM: Homo sapiens

<400> SEQUENCE: 22
ccaggcggat aatatccagt aaggcg                                              26

<210> SEQ ID NO 23
<211> LENGTH: 26
<212> TYPE: DNA
<213> ORGANISM: Homo sapiens

<400> SEQUENCE: 23
ccagactgat aatgtccagt aaggca                                              26

<210> SEQ ID NO 24
<211> LENGTH: 26
<212> TYPE: DNA
<213> ORGANISM: Homo sapiens

<400> SEQUENCE: 24
ccagactgat aatatccagt aaggtg                                              26

<210> SEQ ID NO 25
<211> LENGTH: 26
<212> TYPE: DNA
<213> ORGANISM: Homo sapiens

<400> SEQUENCE: 25
ccaagctgat aatatccagt gaggca                                              26

<210> SEQ ID NO 26
<211> LENGTH: 26
<212> TYPE: DNA
<213> ORGANISM: Homo sapiens

<400> SEQUENCE: 26
ccaagctgat aacatccagt aagtca                                              26

<210> SEQ ID NO 27
<211> LENGTH: 26
<212> TYPE: DNA
<213> ORGANISM: Homo sapiens

<400> SEQUENCE: 27
ccaaactgat aatatccagt aagtta                                              26

<210> SEQ ID NO 28
<211> LENGTH: 26
<212> TYPE: DNA
```

```
<213> ORGANISM: Homo sapiens

<400> SEQUENCE: 28
ccaaactgat aatatccagt aaggta                                            26
```

METHOD FOR HAPLOTYPE ANALYSIS

CROSS REFERENCE TO RELATED APPLICATIONS

This application claims priority to U.S. Provisional Application Ser. No. 60/402,439, filed on Aug. 9, 2002, the content of which is incorporated herein by reference in its entirety.

FIELD OF THE INVENTION

The invention generally relates to bioinformatics and haplotype inference. More particularly, the invention relates to a method for haplotype frequency estimation and inference.

BACKGROUND OF THE INVENTION

Haplotypes provide a powerful tool for today's geneticists and gene hunters. The use of single nucleotide polymorphisms ("SNPs") for haplotype-based disease gene mapping and identification is becoming increasingly popular. A significant practical problem associated with SNP haplotype-based gene mapping is related to phase determination. A first step in determining a haplotype from SNP data is to obtain raw sequence (or genotype) data from an individual or collection of individuals by sequencing (or genotyping) their DNA. When proceeding from genomic DNA, two alleles of the target locus are normally present, so the sequencing procedure yields signal for both alleles. An individual who is homozygous at the locus will have one sequence present because the sequence for the two alleles is identical. If the individual is heterozygous at the locus, the sequences at the two alleles will not be identical and there will be ambiguity at polymorphic sites within the locus. For illustration purposes, consider two alleles having the sequence of SEQ ID NO: 1 ATTTGGCCTA and SEQ ID NO: 2 ATCTGGGCTT, at the third position there is either a T or a C, at the seventh position there is either a G or a C, and at the tenth position there is either an A or a T. Thus, the haplotype of the first allele is characterized by TGA at the third, seventh, and tenth positions and the haplotype at the second allele is CCT at the respective positions. The phase problem stems from the fact that the sequencing procedure cannot distinguish between the T and C at the third position, the G or C at the seventh position, and the A and T at the tenth position. There is ambiguity in the raw data. Based only on the raw data, any permutation of the genotypes for the alleles such as TCT, TGT, CGA, TCA, and CCA, can potentially be the naturally occurring haplotype. Resolution of the naturally occurring haplotype can be accomplished by a variety of molecular haplotyping methods including haplotyping of close relatives, allele specific long range PCR, and the such, but these procedures are typically difficult to implement in a cost effective, efficient manner.

Alternatively, in silico haplotype-determination methods have found increasing utility in view of the difficulties related to the empirical experimental determinations. Three general classes of computer implemented haplotype-determination methods are currently available based on parsimony, Bayesian, and expectation-maximum strategies. A parsimony based method relies on a known phased haplotype to generate the haplotypes from a group of genotypes. Parsimony type methods are based on the assumption that the "correct" set of haplotypes that explain a dataset of genotypes is the one that requires the least number of haplotypes. Such a parsimony based method can be implemented according to Clark's algorithm (Clark *Mol. Bio. Evo.* 7:111-122 (1990)). Clark's method is only feasible when the dataset contains a sufficient number of homozygotes. A Bayesian type approach involves a stochastic search strategy to determine haplotypes (Stephens et al. *Am. J. Hum. Gen.* 68:978-989 (2001); Niu et al. *Am. J. Hum. Gen.* 70:157-169 (2002)). Another method involves an expectation-maximum analysis (EM). The EM analysis involves an initial guess at the haplotype frequencies and an optimization of the log-likelihood function through iterative updates of the frequency estimation.

The EM method relates back to a gene counting method devised by Ceppellini et al. (*Annals Hum. Gen.* 20:97-115 (1955)). Ceppellini et al. solved the problem of obtaining maximum likelihood estimates, "MLEs", for allele frequencies when the alleles are not expressed codominantly. In the canonical example, frequencies for the alleles of the ABO blood group system are obtained despite O being recessive to both A and B. This is done by allocating the count of individuals with blood type a partially to each of the genotypes AA and AO, with the share being determined by an initial guess at the relative frequencies of the A and O alleles.

Given the inferred genotype counts, it is straightforward to get MLEs of allele frequencies. With these new allele frequency estimates the count for type a individuals is reallocated, which leads to new allele frequency estimates and so on. The method is performed similarly with type b individuals. By iterating through this process the MLEs of the allele frequencies are obtained, given the incomplete information provided by the blood group phenotypes. Dempster et al. (*J. Roy. Stat. Soc., Ser. B*, 39:1-38 (1977)) provided considerable generalization of this method to what is now the well-known EM algorithm. Gene counting was applied to the problem of estimating haplotype frequencies from observations of genotypes at proximal loci. See, e.g., Excoffier & Slatkin *Mol. Bio. Evo.* 12:921-927 (1995); Hawley & Kidd *J: Hered.* 86:772-789 (1995), Long et al. *Am. J. Hum. Gen.* 56:799-810 (1995).

A substantial problem with the EM method is that the computational requirements of current implementations grow exponentially as the number of loci grows. For instance, in considering k diallelic loci there are $2^k$ possible haplotypes, $2^{k-1}(2^k+1)$ possible unordered haplotype pairs, and $3^k$ possible sets of genotype observations. In some cases, like a very large sample and a few loci, all haplotypes might be observed, or at least cannot be shown not to occur given the incomplete information provided by the genotypes. However, even with moderately sized samples and a moderate number of loci, it is clear that many haplotypes do not accumulate any of the partial counts derived from the genotype counts. The method presented herein makes use of this by building up the set of haplotypes that have non-zero counts or counts above a minimum threshold and then carrying out the EM algorithm using only these haplotypes, and the haplotype pairs and genotype lists derived from them. In most cases the number of haplotypes required is very small compared with the number of all possible haplotypes. Clearly, the total number of haplotypes that can actually exist in a sample cannot be more than twice the number of individuals and will typically be very much smaller. Even with the extra haplotypes that have to be considered due to incomplete information, the total that is needed grows approximately linearly with the size of the sample, rather than exponentially with the number of loci.

SUMMARY OF THE INVENTION

The invention generally relates to haplotype determination. The invention provides methods for haplotype determination, a computer system for haplotype determination, a database comprising haplotypes determined by the methods of the invention, computer programs for implementing the method, internet nodes for accessing a database comprising haplotypes determined by the method, and internet nodes for determining haplotypes according to the method of the invention.

The invention can be used for analysis and determination of haplotypes. The method of the invention can be used to predict haplotypes from a set of unphased genotypes. The method is particularly efficient for inferring haplotypes. The invention generally involves providing an unphased collection, or set, of genotypes for one or more genetic loci having at least three polymorphic markers. A set of potential haplotypes is determined for at least two polymorphic marker sites in the collection of unphased genotypes. The estimated frequency of occurrence for each potential haplotype is arbitrary assigned (i.e., randomly) or assumed to be equal (or nearly equal). At least one iteration of the EM algorithm is then performed on the set of potential haplotypes. Any haplotype in the set of potential haplotypes having a sufficiently low MLE is removed from consideration in the next round of analysis in which at least one additional marker or locus is considered. The method advantageously eliminates any potential haplotypes whose MLE is zero, or sufficiently low, at an early stage. A dramatic increase in the efficiency of the analysis is realized by eliminating potential haplotypes whose MLE is zero, or sufficiently low, at an early stage of the analysis. This method allows haplotype analysis to be performed on previously unrealizable numbers of polymorphic marker sites.

In an embodiment of the invention, a method for haplotype inference is provided that comprises: (A) performing at least one EM iteration on a first subset of polymorphic marker sites obtained from a set of polymorphic sites in a collection of genotypes; (B) removing from further consideration any potential haplotype whose MLE is sufficiently low to give a set of remaining haplotypes; (C) adding at least one other polymorphic marker site to the set of remaining haplotypes to give a second set of haplotypes; and (D) performing at least one iteration of EM on the second set of haplotypes to infer the haplotypes.

In another embodiment of the invention, a method for limiting the number of potential haplotypes present in a set of unphased genotypes is provided that comprises: (A) providing a set of unphased genotypes from a plurality of individuals wherein the set of unphased genotypes comprises at least three polymorphic sites; (B) predicting the MLE of all potential haplotypes for at least two of the polymorphic marker sites in the set of unphased genotypes; (C) removing from consideration any potential haplotypes that have a sufficiently low MLE to give a set of remaining potential haplotypes; (D) providing a second set of potential haplotypes from the set of remaining haplotypes by adding at least one other polymorphic site to the set of remaining haplotypes; and (E) removing from the second set of potential haplotypes any potential haplotypes whose MLE is sufficiently low, thereby limiting the number of potential haplotypes present in a set of unphased genotypes.

In yet another embodiment of the invention, a method for predicting the estimated frequency of haplotypes in a population, for at least one locus having at least three polymorphic marker sites, is provided that comprises: (A) determining the MLE of a set of potential haplotypes constructed from at least two polymorphic marker sites in the at least one locus; (B) removing from consideration any potential haplotypes having a sufficiently low MLE, to give a reduced set of potential haplotypes; and (C) predicting the MLE of haplotypes obtained from combining the reduced set of potential haplotypes with at least one additional polymorphic site, thereby predicting the estimated frequency of haplotypes in the population.

In one embodiment, the invention provides a method for producing a set of canonical haplotypes from a set of unphased genotypes for at least one locus that comprises: (A) providing a set of unphased genotypes having at least three polymorphic marker sites said set of unphased genotypes corresponding to a set of potential haplotypes; (B) considering the MLE of sub-haplotypes constructed from at least two polymorphic sites in the set of unphased genotypes; and (C) producing a reduced set of potential haplotypes from the set of potential haplotypes by removing any haplotypes containing sub-haplotypes whose MLE is sufficiently low, to give a set of canonical haplotypes.

In still another embodiment, the invention provides a method for determining a subject haplotype from an unphased genotype comprising: (1) generating a set of canonical haplotypes from a plurality of unphased genotypes wherein the canonical haplotypes are determined by, (A), providing a set of unphased genotypes having at least three polymorphic marker sites, said set of unphased genotypes corresponding to a set of potential haplotypes, (B), considering the MLE of sub-haplotypes constructed from at least two polymorphic sites from the set of unphased genotypes, (C), producing a set of canonical haplotypes by removing any potential haplotypes containing sub-haplotypes having a sufficiently low MLE to give a set of canonical haplotypes; and (2) comparing the unphased genotype to the canonical haplotypes to give the subject haplotype.

In one embodiment, the invention provides a method for haplotype determination comprising: (A) providing a first set of loci having three or more polymorphic marker sites for a plurality of individuals; (B) selecting and removing any two loci from the first set of loci; (C) creating a new locus wherein the set of haplotypes of the new locus is the product of the two loci removed in step (B); (D) assigning to the haplotypes of the new set of haplotypes a uniform, or nearly uniform initial haplotype frequency; (E) performing at least one iteration of EM on the new locus using the genotypes for the markers that are in the new locus; (F) removing from the new set of haplotypes any haplotype whose current estimate of frequency is sufficiently low from the new set of haplotypes; and (G) repeat steps (B)-(F) until the first set of loci is empty, thereby determining the haplotypes In another embodiment, the invention provides a method for determining haplotype phases comprising: (A) providing a set of loci that contains the k loci corresponding to the original k markers, (B) selecting and removing any two loci from the set of loci, (C) creating a new locus whose haplotype is the product of the two loci removed from the original set of loci, (D) performing at least one iteration of EM on the new locus using the genotypes for markers that are in the new locus, (E) removing any haplotype from set whose current estimate of frequency is sufficiently low, and (F) repeating steps (B)-(E) until the original set of loci is empty, thereby determining the phase of the haplotypes.

In still yet another embodiment, the invention provides a method for estimating the frequency of haplotypes and inferring haplotypes from genotypes for a set of individuals that comprises: (A) providing a set of genotypes for a locus obtained from at least two individuals, said locus comprising three or more polymorphic markers; (B) combining two markers, a marker and a locus, or two loci from the set of genotypes to give a new locus; (C) removing any haplotypes from the new locus that have a sufficiently low MLE after at least one iteration of EM on the new locus; (D) repeating from step (B) until all the genotypes have been combined into a final locus; and (F) running EM to convergence on the final locus to give the estimated frequency of haplotypes and inferred haplotypes from the set of genotypes.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

Current implementations of EM analysis for estimating haplotype frequencies from genotypes on proximal loci require computational resources that grow as $nh_k^2$ where n is the number of individuals genotyped and h is the number of haplotypes possible on k loci. For diallelic loci $h_k=2^k$. The present invention provides an approach whose computational requirement grows as $nh^2$, where h is the largest number of loci at which an individual in the sample is heterozygous.

The invention relates to the discovery that haplotypes can be predicted more efficiently by removing any sub-haplotypes having a sufficiently low MLE from consideration from the super-haplotype. For example, consider the number of possible haplotypes for two linked loci. This is equal to the product of the number of alleles at the two loci. However, if in some particular sample of genotypes at these loci, an allele at either locus is absent, it can be eliminated from consideration at the locus and also from consideration in the haplotype. Thus, the number of haplotypes that need to be considered is reduced. Thus, the method exploits this observation by breaking up the required haplotypes into sub-haplotypes. The method is not a parsimonious one since it does not involve limiting the set of haplotypes required to explain the genotypes. The method is also not an approximation of the EM method. Rather, it is an efficient way of detecting and eliminating at an early stage of analysis all haplotypes whose MLE is sufficiently low or zero.

The method of the invention can be used to predict haplotypes and/or their estimated frequency of occurrence. The method of the invention utilizes a set of loci comprised of at least three polymorphic marker sites from at least two individuals. Haplotype prediction according to the method involves removing two loci from the set, creating a new locus from the product of the two removed loci and performing one or more EM iterations on the new locus using the genotypes for the markers in the new locus. All haplotypes having a sufficiently low estimate of frequency are removed from further consideration. The process is repeated until the original set of loci is empty. Thus, all haplotypes whose estimate of frequency is sufficiently low are removed, and a set of haplotypes (and/or their estimated frequency of occurrence) which is a subset of all the possible haplotypes, is provided. The method is particularly useful for analyzing datasets containing numerous polymorphic marker sites for many individuals. The method is also capable of analyzing incomplete datasets where genotype information is missing for at least one locus for at least one individual.

The inventive methods are capable of analyzing, inferring, determining, and phasing haplotypes from raw data genotype data. Optionally, the methods, software, and systems of the invention can also accommodate additional input data including empirically determined haplotypes, haplotypes of relatives and family members, degree of relatedness, and the such. Such additional input data is considered within the context of the inventive method and serves to further refine the analysis of the haplotypes. An ordinary skilled artisan is capable of implementing the method of the invention in conjunction with additional input data.

As used herein, the term "haplotype" means a combination of genetic (nucleotide) variants in a region of genomic DNA on a single chromosome found in an individual or an mRNA derived from a single chromosome found in an individual. Thus, a haplotype includes a number of genetically linked "nucleotide variant markers" or "polymorphic marker sites" which are typically inherited together as a unit. The number of markers in a haplotype should be at least 2, preferably at least 3, and more preferably at least 4. The term "potential haplotypes" is intended to encompass any haplotypes that can be constructed from a combination of two or more polymorphic markers.

As used herein, the term "canonical haplotypes" generally refers to the haplotypes that commonly exist in a defined heterogeneous population of a subject species (a heterogeneous subject population). A "canonical haplotype collection" means a collection of canonical haplotypes representative of all canonical haplotypes in a defined heterogeneous subject population. Typically, a canonical haplotype collection consists of canonical haplotypes having a frequency in the defined population of 1.5% or higher, preferably 1% or higher, or 0.5% or higher, or at least 0.1%. As will be apparent to skilled artisans, in determining the desirable lower limit of a canonical haplotype frequency in a canonical haplotype collection, one should take into consideration many different factors including the diversity of a heterogeneous population, the size of the chromosomal region covered by the haplotype, and the number of nucleotide variant markers contained within a particular haplotype of interest. For example, the more diverse a population is, the smaller the lower haplotype frequency limit should be. Also, the more nucleotide variant markers are contained within a haplotype of interest, the smaller the lower haplotype frequency limit should be. For purposes of the method of the present invention, it is preferably that the lower limit is set such that almost all the common known haplotypes in a particular chromosomal DNA region are included while rare haplotypes in the region representing large genomic rearrangements are excluded.

As used herein, the term "allele" refers generally to one copy of a naturally occurring DNA region in a diploid subject. "Gene allele" refers generally to one copy of a naturally occurring gene in a diploid subject. A diploid subject has two chromosomes and usually two copies of a particular DNA region or gene, and thus two haplotypes of any region of the gene and two alleles of any polymorphic site within the gene. As used herein, the term "subject haplotype" means a haplotype of an individual subject being studied.

As used herein, the term "marker" refers to a site of genetic polymorphism. Examples of markers include, but are not limited to, single nucleotide polymorphisms (SNPs), restriction fragment length polymorphisms (RFLPs), and microsatellite repeats.

As used herein, the term "plurality of individuals" refers to at least two individuals of a particular species. For example, the term "a plurality of individuals" encompasses 2, 3, 4, 5, 6, 7, 8, 9, 10, 15, 20, 25, 30, 40, 50 or more individual organisms such as animal organisms including, humans, mice, rats, cows, worms, fruit flies, zebrafish, and plant organisms such as maize, rice, *Arabidopisis*, soy, and so on. "Individual" is used in the general context of being genetically non-identical.

As used herein, the term "locus" refers to genetic information, i.e, DNA, having at least one polymorphic marker site.

As used herein, the term "sufficiently low MLE" refers to an MLE that indicates that the trait, i.e., haplotype, is not likely to exist in the population being analyzed. Preferably, a sufficiently low MLE is zero, or approximately zero, or approaches zero as more data is considered in the analysis. A sufficiently low MLE is recognizable by an ordinary skilled artisan by considering such factors as the nature and quality of the input dataset, and the purpose of the analysis. For example, for some analyses, a sufficiently low MLE may be ten percent of the frequency of occurrence of a particular haplotype in a dataset having k samples: $(0.1)(1/(2k))$. A sufficiently low MLE can be, e.g., 1% of the frequency of occurrence of a particular haplotype in a dataset having k samples, 5% of the frequency of occurrence of a particular haplotype in a dataset having k samples, 15 % of the frequency of occurrence of a particular haplotype in a dataset having k samples.

As used herein, the term "super-haplotype" refers to a haplotype, or collection of haplotypes, that can be constructed from the product of two haplotypes and is a term of degree in relation to "sub-haplotype". "Super-haplotype" can also refer to the haplotypes representative of a set of unphased genotypes. Two or more sub-haplotypes can be combined to give a super-haplotype and a super-haplotype can be decomposed into two or more sub-haplotypes.

As used herein, the term "genotype" refers to the unordered pair of alleles. Thus, "genotype" can mean the nucleotide characters at a particular nucleotide variant marker in either one allele or both alleles of a gene. When the term "unphased genotypes" is used in connection with a biallelic gene, unphased genotypes for a particular marker can be expressed, e.g., in the form of X/Y, wherein X and Y are nucleotide symbols (e.g., A, T, G, C). Methods for determining "unphased genotypes" are generally known in the art. For example, diploid DNA can be sequenced in a nucleotide variant marker region with sequencing primers that are not allele specific.

The invention can be exemplified as follows. Let a locus be a combination of one or more markers. The alleles, or haplotypes, at a locus are in general, in the absence of data on relatives, unobservable because one cannot observe the phase of the component markers. Given two loci, $l_1$ and $l_2$, that are made up of two non-overlapping sets of markers, define the product $l_3=l_1\times l_2$ to be the locus made up of all the markers in $l_1$ and $l_2$. The set of possible haplotypes at $l_3$ will be the product of the sets of haplotypes at $l_1$ and $l_2$. The set of haplotypes actually present at $l_3$ will be a subset of this product. The haplotypes at $l_1$ or $l_2$ are sub-haplotypes of those at $l_3$. Those at $l_3$ are super-haplotypes of those at $l_1$ and $l_2$. The problem is to infer the frequencies of haplotypes at the locus made up of k, for example, markers, given a set of genotypes at those markers. The method is as follows: (A) initialize a set of loci L to contain the k loci corresponding to the original k markers; (B) arbitrarily choose any two loci $l_1$ and $l_2$ from L and remove them from the set L; (C) create a new locus $l=l_1\times l_2$ whose haplotypes are the product of those in $l_1$ and $l_2$; (D) assign initial haplotype frequencies (e.g., can be random values or uniform, or nearly uniform) and run at least one round of the EM algorithm on l, considering only the genotypes for markers that are in l; (E) remove from the set of haplotypes of l any whose current estimate of frequency is sufficiently low. If L is not empty, add l to L and iterate from step (B) above. If L is empty, l contains all the initial loci, and all the haplotypes whose frequency MLE is not identically zero. Run EM on l to convergence to obtain frequency MLEs. Since the haplotypes removed at step (E) have a sufficiently low MLE, any super-haplotype that contains that set of alleles at those markers will also have a sufficiently low MLE. Thus, the set of haplotypes, l, that is arrived at will be independent of the order in which the loci were incorporated and will contain all haplotypes having a non-zero MLE (or non-sufficiently low MLE) if EM were run on the full $2^k$ haplotypes.

Loci can be incorporated in several ways and the results are independent of the order in which the loci are combined. In a preferred aspect, the original markers are added chromosomal order. The methods of the invention advantageously allow for the consideration datasets that were intractable by other haplotype analysis means, e.g., datasets containing a large number of polymorphic sites and/or datasets sets with missing data points. A variety of implementations of the inventive method are provided as follows.

The invention provides a method for haplotype inference comprising steps (A)-(D) described below. Step (A) involves performing one or more EM iterations on a first subset of polymorphic marker sites obtained from a set of polymorphic sites in a collection of genotypes. Next, in step (B), any potential haplotypes with a sufficiently low MLE are removed from further consideration to give a set of remaining haplotypes. In step (C) at least one other polymorphic marker site from the collection of genotypes is combined with the set of remaining haplotypes to give a second set of haplotypes. One or more iterations of EM are performed on the second set of haplotypes in step (D) to infer the haplotypes. In a preferred aspect of this embodiment, if all of the genotype observations have not been considered the method is iterated until a sufficient number of genotype observations have been considered to infer the haplotypes. Any combination of new genotype information can be considered during the iterations, including, at least two additional polymorphic marker sites, a polymorphic marker site and a loci, or two loci. Any haplotypes that have a sufficiently low MLE are removed from consideration during the iterations and a set of haplotypes is inferred by performing EM on the final set of haplotypes.

A method for limiting the number of potential haplotypes present in a set of unphased genotypes is provided by the invention. The method of this embodiment starts with providing a set of unphased genotypes. The set of unphased genotypes used in the method is for at least one locus, for a plurality of individuals, and covers at least three polymorphic maker sites. At least two polymorphic marker sites are removed from the set of unphased genotypes and the MLEs of all potential haplotypes obtained from the product of the two or more polymorphic sites that were removed are determined. Any potential haplotypes having a sufficiently low MLE are removed from further consideration to give a set of remaining potential haplotypes. Next, a second set of potential haplotypes, obtained from combining the set of remaining haplotypes with at least one other polymorphic site is provided. One or more iterations of EM are performed on the second set of potential haplotypes and those having a sufficiently low MLE are removed, thereby limiting the number of potential haplotypes present in a set of unphased genotypes. Iterations of the method are run to include additional polymorphic marker sites. Such iterations can include the analysis of at least two additional polymorphic sites, at least one polymorphic site and a locus, or at least two loci. After considering a sufficient amount of unphased genotype information, EM analysis of the remaining haplotypes can be performed to give their estimated frequency of occurrence. The invention also provides a method for predicting the estimated frequency of haplotypes in a population. According to this method, at least one locus, having at least three polymorphic marker sites, for two or more individuals is analyzed. The MLEs of a set of potential haplotypes is obtained by performing EM analysis on a combination of at least two polymorphic marker sites in the locus. Any potential haplotypes having a sufficiently low MLE are removed from consideration to give a reduced set of potential haplotypes. Next, MLEs of haplotypes obtained from combining the reduced set of potential haplotypes with at least one additional polymorphic site are determined, thereby predicting the estimated frequency of haplotypes in the population. Preferably, the process of performing EM on haplotypes obtained from at least two or more markers, and removing haplotypes with a sufficiently low MLE, is iterated until all the polymorphic marker sites or a sufficient number of sites have been considered.

The invention further provides a method for producing a set of canonical haplotypes from a set of unphased genotypes for at least one locus. The method first involves providing a set of unphased genotypes having at least three polymorphic markers that corresponds to a set of potential haplotypes. Next, the MLEs of sub-haplotypes constructed from at least two polymorphic sites are determined. A reduced set of potential haplotypes is obtained from the set of potential haplotypes by removing any haplotypes containing sub-haplotypes whose MLE is sufficiently low, to give a set of canonical haplotypes. Removal of any haplotypes having a sufficiently low MLE can be accomplished by iterative consideration of at least one additional marker or locus. Thus, a set of canonical haplotypes is produced that does not have sub-haplotypes with sufficiently low, or zero, MLEs.

A method for determining a subject haplotype from an unphased genotype is provided according to one aspect of the invention. A subject haplotype can be determined by generating a set of canonical haplotypes from a plurality of unphased genotypes according to a method of the instant invention capable of predicting, inferring, phasing, or estimating haplotypes. For example, canonical haplotypes can be determined by providing a set of unphased genotypes having at least three polymorphic marker sites that correspond to a set of potential haplotypes. Next, the MLEs of sub-haplotypes constructed from at least two polymorphic sites are determined. A set of canonical haplotypes is produced by removing any potential haplotypes containing sub-haplotypes having a sufficiently low MLE. Once a set of canonical haplotypes are provided according to the methods of the invention, the unphased subject genotype is compared to the canonical haplotypes to give the subject haplotype.

The invention provides a method for haplotype determination. According to this embodiment, a first set of loci, containing three or more markers, is provided for a plurality of individuals. Any two loci from the first set of loci are selected and removed from the first set of loci. A new locus is created where the set of haplotypes of the new locus is the product of the two loci removed in the previous step. The new set of haplotypes in the new locus is assigned a uniform, or nearly uniform, initial haplotype frequency estimate and one or more iterations of EM are performed on the new locus using the genotypes for the markers in the new locus. Any haplotype whose current estimate of frequency is sufficiently low during the EM analysis is removed from the new set of haplotypes. Additional markers or loci are considered using the method until the first set of loci is empty and the haplotypes present in the first set of loci are determined. The invention provides a method for determining haplotype phases. Accordingly, a set of loci that contains the k loci corresponding to the original k markers is provided and any two loci are removed from the set of loci. A new locus whose haplotype is the product of the two loci removed from the original set of loci is created and at least one iteration of EM is performed on the new locus using the genotypes for markers that are in the new locus. Any haplotype in the new locus whose current estimate of frequency is sufficiently low is removed from consideration. Iterations of creating a new locus and removing haplotypes with a sufficiently low MLE are performed until the original set of loci is empty. A set of phased haplotypes is obtained that corresponds to the original unphased genotype data. EM analysis on the set of haplotypes thus obtained provides their expected frequency of occurrence.

The inventive method can be implemented with the use of other haplotype estimation/inference algorithms during the iterative analysis of the loci and markers, and/or the final analysis of the complete set of genotype observations. The use of EM is preferred.

The method of the present invention can also be embodied in computer program products and used in computer- or internet-based systems. Accordingly, another aspect of the present invention relates to a computer program product comprising a computer-usable medium having computer-readable program code or instructions embodied thereon for enabling a processor to carry out the method of the present invention. Typically, the computer-readable program code in the computer program product of the invention enables a computing system to receive information representative of unphased genotypes at a plurality of nucleotide variant markers in a locus of interest of a diploid subject. In addition, the computer-readable program code in the computer program product also enables the comparison of the unphased genotypes with canonical haplotypes within a canonical haplotype collection.

The computer-readable program code can be stored on a variety of media including, but not limited to, floppy disks hard disks, CD-ROMs, RAM, and the such. The computer-readable program code or software can be written in any language capable of implementing the methods. Programming languages that can be used in the applications of the present invention, include, but are not limited to, JAVA, C, C++, Fortran, Perl, Pascal, and so on. The selection of storage device and language depends on the specific application of the invention is readily apparent to an ordinary artisan. In one embodiment, the computer-readable program code enables the computer system incorporating or running the computer program product or the computer-readable program code therein to receive or generate information on canonical haplotypes and receive information on unphased genotypes of a tested subject. The computer-readable program code then enables comparison between the unphased genotypes and the canonical haplotype pairs to determine if a canonical haplotype pair matches the unphased genotypes, i.e., if the unphased genotypes can be reduced to a canonical haplotype.

Figure 1:
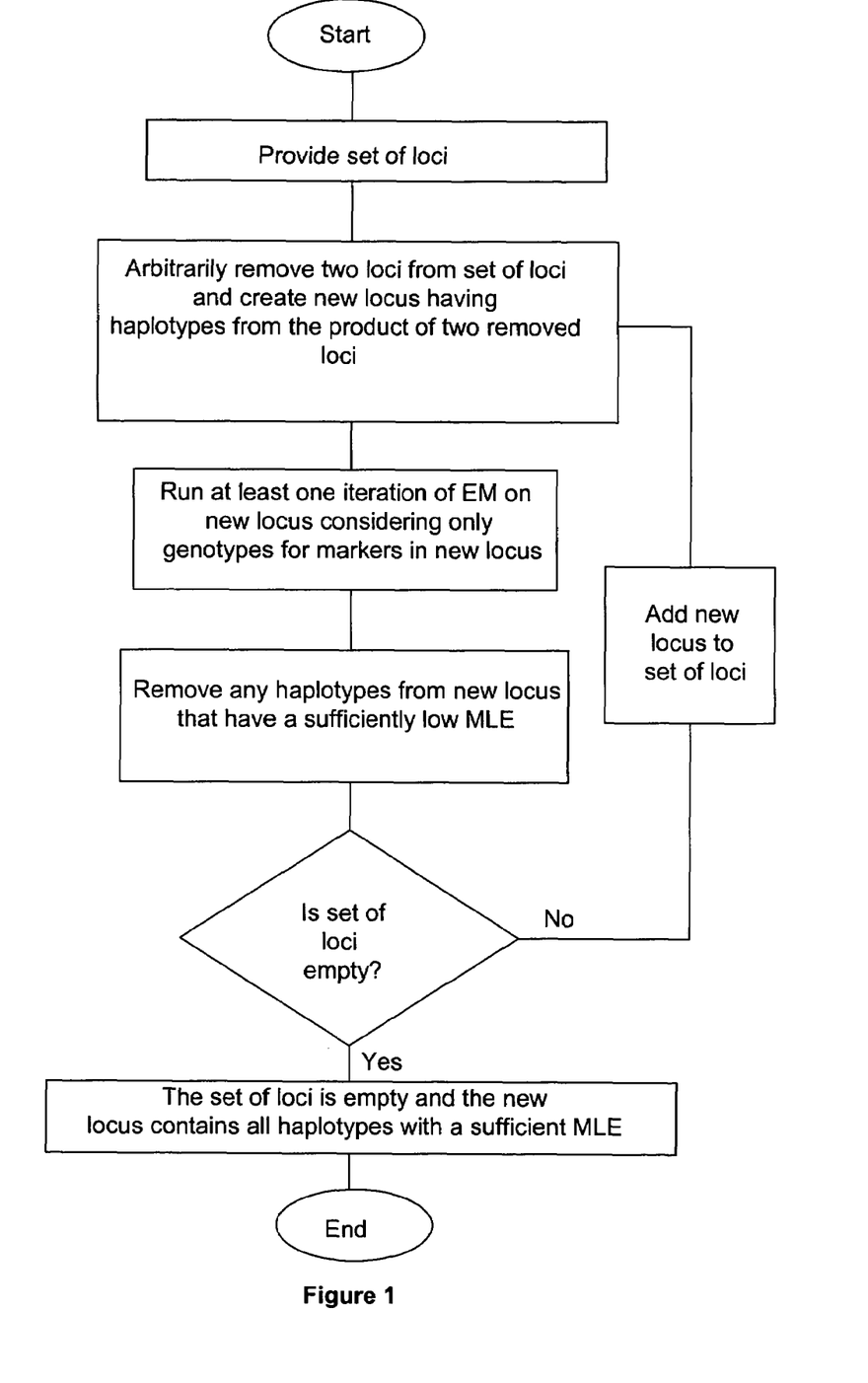
FIG. 1 illustrates a flow chart for an embodiment of the method of the invention.

FIG. 1 is a flowchart illustration of an embodiment of the methods and program products according to the invention. The first step in this embodiment is to provide a set of genotype observations (set of loci). The genotype observations can be made, e.g., by isolating DNA from individuals, followed by sequencing of a particular region or gene. The minimal genotype observations for use in the method are at least two individuals with three polymorphic sites. Next, two loci are arbitrarily removed from the genotype observations and a new locus is created from the product of the two removed loci. The new locus is then subjected to at least one round of EM considering only the genotypes for markers in the new locus and any haplotypes whose MLE is sufficiently low are removed from the new locus. If the set of genotype observations is not empty then another iteration of removing 2 loci from the genotype set, EM on the new locus, and removal of haplotypes with sufficiently low MLEs is performed. If the set of genotype observations is empty, the new locus contains all haplotypes having a sufficient MLE and EM can be run on the new locus to obtain frequency MLEs.

Figure 2:
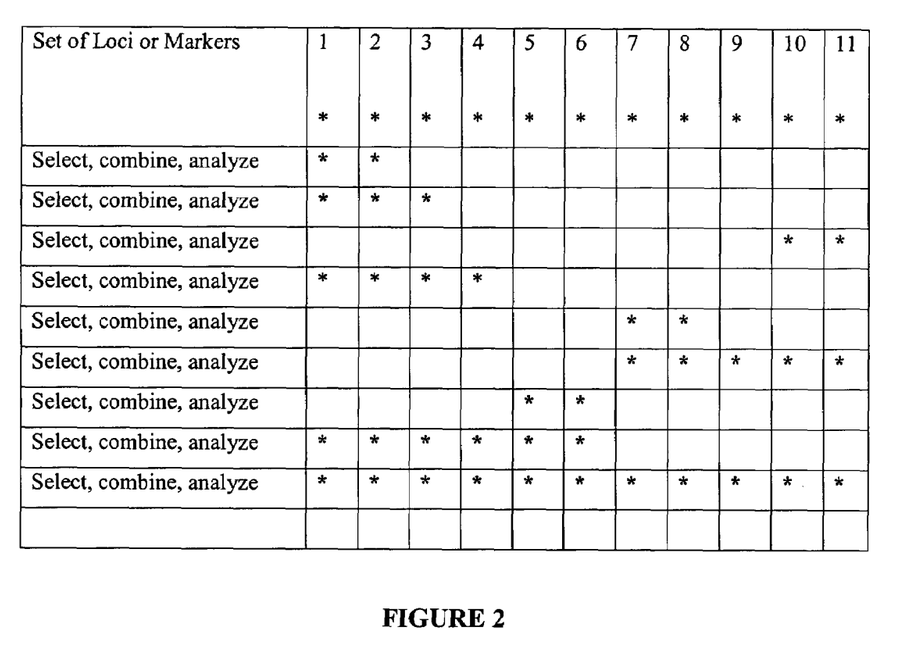
FIG. 2 shows an example of how genotype data can be combined and analyzed according to an embodiment of the invention.

FIG. 2 is a chart exemplifying an aspect of the method of the invention. FIG. 2 is a non-limiting illustration of how data can be combined and considered according to the invention. In this figure, one starts with a set of eleven loci or markers. In the first round loci 1 and 2 are combined and analyzed to remove any sub-haplotypes with a sufficiently low MLE. In the next round, locus 3 is added to 1 and 2, and any haplotypes having a sufficiently low MLE are removed. Continuing on, loci 10 and 11 are considered and those haplotypes with a sufficiently low MLE are removed. The process is iterated until all the loci or markers have been considered. The estimated frequency of occurrence of the haplotypes in the final set is determined by performing EM on the remaining haplotypes.

Figure 3:
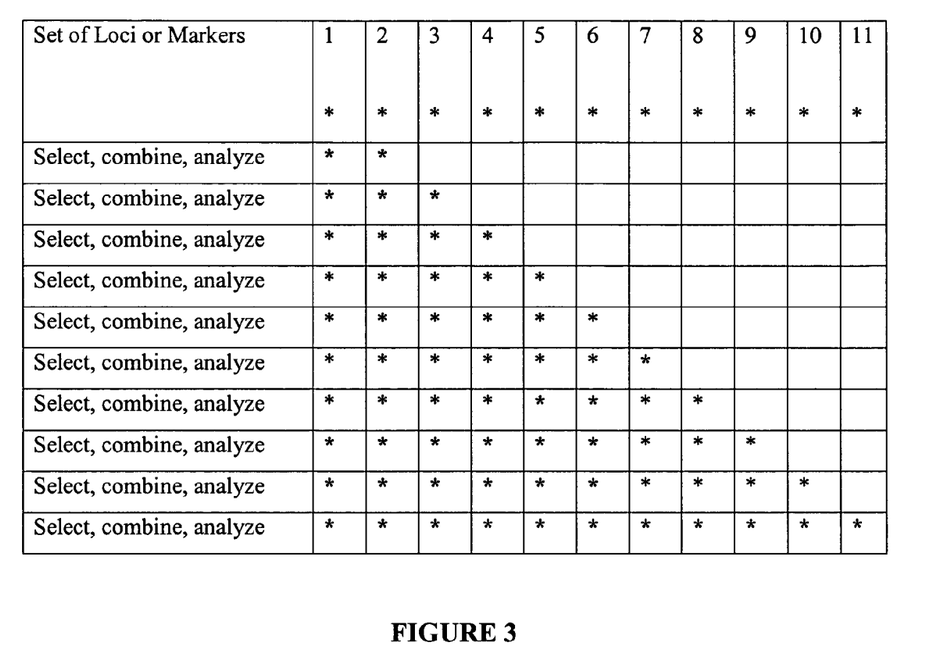
FIG. 3 shows an example of how genotype data can be combined and analyzed according to an embodiment of the invention.

FIG. 3 is a chart exemplifying an aspect of the method of the invention. FIG. 3 is a non-limiting illustration of how data can be combined and considered according to the invention. In this figure, one starts with a set of eleven loci or markers. In the first round loci 1 and 2 are combined and analyzed to remove any sub-haplotypes with a sufficiently low MLE. In the next round, locus 3 is added to 1 and 2, and any haplotypes having a sufficiently low MLE are removed. The loci or markers are added one at a time, the new potential haplotypes are considered, and those haplotypes with a sufficiently low MLE are removed. The process is iterated until all the loci or markers have been considered. The estimated frequency of occurrence of the haplotypes in the final set is determined by performing EM on the remaining haplotypes.

It will be understood that each block or step of the flowcharts illustration and combinations of blocks in the flowcharts can be implemented by computer program instructions. These computer program instructions may be loaded onto a computer or other programmable apparatus to produce a machine, such that the instructions which execute on the computer or other programmable apparatus create means for implementing the functions specified in the flowcharts or step(s). These computer program instructions may also be stored in a computer-readable memory or medium that can direct a computer or other programmable apparatus to function in a particular manner, such that the instructions stored in the computer-readable memory or medium produce an article of manufacture including instruction means that implement the function specified in the flowchart(s) or step(s). The computer program instructions may also be loaded onto a computer or other programmable apparatus to cause a series of operational steps to be performed on the computer or other programmable apparatus to produce a computer implemented process such that the instructions that execute on the computer or other programmable apparatus provide steps for implementing the functions specified in the flowchart(s) or step(s).

Accordingly, the flowcharts support combinations of means for performing the specified functions, combinations of steps for performing the specified functions and program instruction means for performing the specified functions. It will also be understood that each step of the flowcharts and combinations of steps in flowcharts can be implemented by special purpose hardware-based computer systems which perform the specified functions or steps, or combinations of special purpose hardware and computer instructions.

The system can include a processor connected to interface module(s) or database(s), or physically separated from, but electrically connected to the interface module(s) or database(s). In either instance, it must be understood that the processor may consist of any number of devices. The processor may be a data processing device, such as a microprocessor or microcontroller or a central processing unit. The processor could be another logic device such as a DMA (Direct Memory Access) processor, an integrated communication processor device, a custom VLSI (Very Large Scale Integration) device, or an ASIC (Application Specific Integrated Circuit) device. In addition, the processor can be any other type of analog or digital circuitry that is designed to perform the processing functions described herein.

The invention is intended to encompass various embodiments of internet applications of the present invention, e.g., an internet node or intranet node. Such a node should include an interface module.

The system can have computer instructions means for enabling the processor to generate a canonical haplotype collection from information representative of an unphased genotype collection. The system can also contain computer instruction means to cause the processor to compare a subject unphased genotype with the canonical haplotype collection. The system can also contain a computer instructions means to cause the processor to compare unphased genotypes with a canonical haplotype collection. The system should display the comparison results through one of the two interface modules described above or a third interface module or a display device integrated with the processor, or alternatively, physically separated but electrically connected to the processor.

Figure 4:
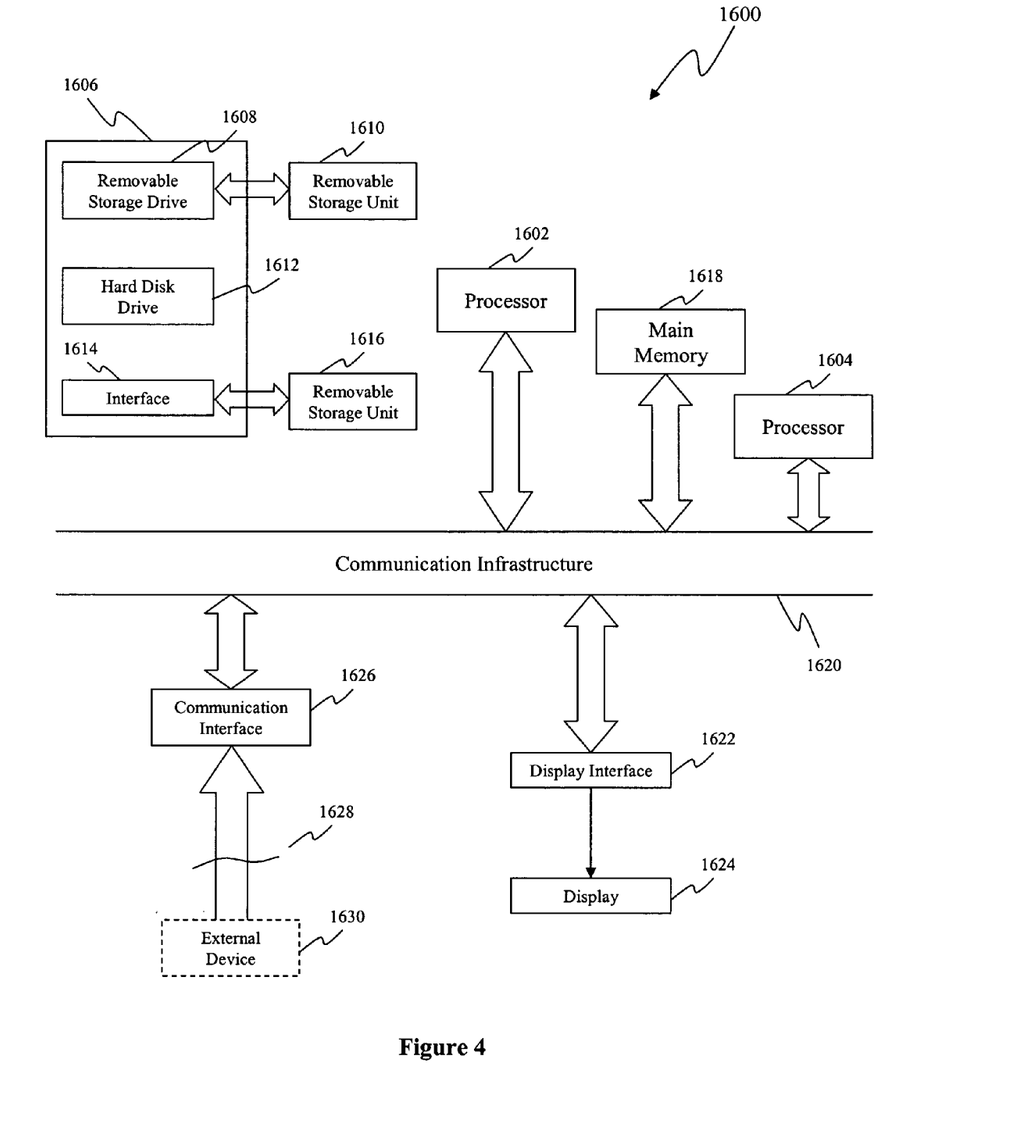
FIG. 4 shows an example of a schematic diagram illustrating a computing system for executing the instructions from the computer program products or computer-readable codes of the present invention.

Accordingly, in accordance with yet another aspect, a computer system is provided for executing the instructions from the computer program products of the present invention. An embodiment of the system is shown in FIG. 4. Referring now to FIG. 4, system 1600 includes one or more processors, such as processors 1602 and 1604. The processors can be used to execute software or computer-readable instruction codes implementing the method of the present invention described above. It must be understood that the processor may consist of any number of devices. The processor may be a data processing device, such as a microprocessor or microcontroller or a central processing unit. The processor could be another logic device such as a DMA (Direct Memory Access) processor, an integrated communication processor device, a custom VLSI (Very Large Scale Integration) device or an ASIC (Application Specific Integrated Circuit) device. In addition, the processor can be any other type of analog or digital circuitry that is designed to perform the processing functions described herein.

Computer system 1600 also includes a main memory 1618, preferably random access memory (RAM). A second memory 1606 may also be included. The secondary memory 1606 may include, e.g., a remove storage drive 1608, which can be in various forms, including but not limited to, a magnetic tape drive, a floppy disk drive, a VCD drive, a DVD drive, an optical disk drive, etc. The removable storage drive 1608 may be compatible with a removable storage unit 1610 such that it can read from and/or write to the removable storage unit 1610. Removable storage units typically include a computer usable storage medium having stored therein computer-readable program codes or instructions and/or computer readable data. Example of removable storage units are well known in the art, including, but not limited to, floppy disks, magnetic tapes, optical disks, and the like.

Preferably, secondary memory 1606 also includes a hard drive 1612, which can be used to store computer readable program codes or instructions, and/or computer readable data.

In addition, as shown in FIG. 4, secondary memory 1606 may further include an interface 1614 and a removable storage unit 1616 that is compatible with interface 1614 such that software, computer readable codes or instructions can be transferred from the removable storage unit 1616 into computer system 1600. Examples of interface-removable storage unit pairs include, e.g., removable memory chips (e.g., EPROMs or PROMs) and sockets associated therewith, program cartridges and cartridge interface and the like.

As shown in FIG. 4, in computer system 1600, processors 1602 and 1604 as well as the main and secondary memories 1618 and 1606 are all operably linked together through communication infrastructure 1620, which may be a communications bus, system board, cross-bar, etc.). Through the communication infrastructure 1620, computer program codes or instructions or computer readable data can be transferred and exchanged.

Additionally, it may also be desirable to exchange data with other devices or systems located distant from the computer system 1600. For this purpose, an internet node or an intranet node including an interface module (also called communications interface) 1626 may be included in computer system 1600 such that computer-readable data (e.g., texts, tables, descriptions, photos, diagrams, etc. in the form of electronic, electromagnetic, optical or other signals), and software or other computer-readable codes or instructions may be transferred back and forth between external device 1630 and computer system 1600. Preferably, a communications path 1628 compatible with the communications interface 1626 is included. As will be apparent to skilled artisans, modems, communication ports, network cards such as Ethernet cards, and newly developed devices for accessing intranet or internet can all be used as the communication interface 1626.

In addition, computer system 1600 can also include a display interface 1622. Through display interface 1622, results of data analysis, e.g., in the forms of graphics, table, text, and the like from communication infrastructure 1620 may be displayed on display unit 1624.

In accordance with the present invention, the computer system implements a computer program or computer-readable codes or instructions to execute the data processing, analysis, comparison and coordination described above in various embodiments of the present invention. As such the computer readable program codes or instructions (i.e., computer instructions means for enabling processor 1602 and/or 1604 to perform the processing, analysis, comparison and/or coordination) may be included in the computer system such as system 1600 directly or through a computer program product as described above. Examples of such computer program products in system 1600 include, e.g., removable storage units 1610 and 1616, a hard disk (not shown) in hard disk drive 1612 and a carrier wave (not shown) which delivers software or computer readable codes or instructions to system 1600 through communication interface 1626 and communication path 1628.

EXAMPLES

Example 1

Haplotype Analysis with Simplified Dataset

Consider 4 markers, each with alleles 0 and 1. Also consider a sample of size 4 that has the observed genotype lists given in table 1, where genotypes 0, 1 and 2 correspond to the number of occurrences of the allele 1 at each locus (0 in table 1 refers to (0,0) 1 refers to (1,0) and 2 refers to (1,1)).

TABLE 1

Raw Data

| Sample | Loci | | | |
|---|---|---|---|---|
| | $l_1$ | $l_2$ | $l_3$ | $l_4$ |
| 1 | 0 | 1 | 2 | 0 |
| 2 | 1 | 0 | 2 | 0 |
| 3 | 1 | 0 | 1 | 0 |
| 4 | 0 | 2 | 0 | 1 |

Pairing up the first two loci and the last two loci we find the frequencies for the sub-haplotypes after one round of EM given in table 2. For example, pairing $l_1$ and $l_2$ for sample 1 ((0,0)×(1,0)) yields (0,1) and (0,0) and gives a count to each of those entries in table 2.

TABLE 2

Initial pairings

| $l_5 = l_1 \times l_2$ Loci 1 and 2 | | $l_6 = l_3 \times l_4$ Loci 3 and 4 | |
|---|---|---|---|
| Haplotype | Count | Haplotype | Count |
| (0, 0) | 3 | (0, 0) | 2 |
| (0, 1) | 3 | (0, 1) | 1 |
| (1, 0) | 2 | (1, 0) | 5 |
| (1, 1) | 0 | (1, 1) | 0 |

Now, combining the two results we have to consider only the 9 haplotypes made from the product of {(0,0),(0,1),(1, 0)} times {(0,0),(0,1),(1,0)}instead of the full 16 haplotypes possible. After one round of EM we get the results in table 3, column 2.

TABLE 3

The full locus $L_7 = l_5 \times l_6$

Frequency estimate after gene counting iteration

| Haplotype | 1 | 10 | 100 | 1000 |
|---|---|---|---|---|
| (0, 0, 0, 0) | 0.0625 | 3.15 × 10-5 | 3.61 × 10$^{-48}$ | 0 |
| (0, 0, 0, 1) | 0 | | | |
| (0, 0, 1, 0) | 0.3125 | 0.374968 | 0.375 | 0.375 |
| (0, 1, 0, 0) | 0.125 | 0.125 | 0.125 | 0.125 |
| (0, 1, 0, 1) | 0.125 | 0.125 | 0.125 | 0.125 |
| (0, 1, 1, 0) | 0.125 | 0.125 | 0.125 | 0.125 |
| (1, 0, 0, 0) | 0.0625 | 0.124968 | 0.125 | 0.125 |
| (1, 0, 0, 1) | 0 | | | |
| (1, 0, 1, 0) | 0.1875 | 0.125032 | 0.125 | 0.125 |

Before gene counting, haplotypes (0,0,0,1) and (1,0,0,1) can be eliminated since they have zero estimated frequency and the original 16 possible haplotypes is reduced to 7. Columns 3, 4 and 5 of table 3 show the frequency estimates after 10, 100 and 1000 gene counting iterations respectively. As can be seen the MLE for the frequency of haplotype (0,0,0,0) goes to zero, but convergence is rather slow. This illustrates that the method of the invention discards only a subset of those haplotypes whose MLE sufficiently low (e.g., is zero).

Note that if we had paired up the first and third loci and the second and fourth we would have obtained counts as in Table 4.

TABLE 4

Alternate initial pairings

| $l_5 = l_1 \times l_3$ Loci 1 and 3 | | $l_6 = l_2 \times l_4$ Loci 2 and 4 | |
|---|---|---|---|
| Haplotype | Count | Haplotype | Count |
| (0, 0) | 2.5 | (0, 0) | 5 |
| (0, 1) | 3.5 | (0, 1) | 0 |
| (1, 0) | 0.5 | (1, 0) | 2 |
| (1, 1) | 1.5 | (1, 1) | 1 |

This reduces the set of haplotypes at the next stage to 12. After one round of gene counting, the same 7 haplotypes are seen that have non-zero MLEs. Although this is not as efficient as the previous pairing, the end result is the same, as can be seen in table 5.

TABLE 5

| Haplotype | Count |
|---|---|
| (0, 0, 0, 0) | 0.5 |
| (0, 1, 0, 0) | 1 |
| (0, 1, 0, 1) | 1 |
| (0, 0, 1, 0) | 2.5 |
| (0, 1, 1, 0) | 1 |
| (0, 1, 1, 1) | 0 |
| (1, 0, 0, 0) | 0.5 |
| (1, 1, 0, 0) | 0 |
| (1, 1, 0, 1) | 0 |
| (1, 0, 1, 0) | 1.5 |
| (1, 1, 1, 0) | 0 |
| (1, 1, 1, 1) | 0 |

Example 2

Haplotype Frequency Estimation and Phasing on Real Dataset

The method is exemplified by haplotype frequency estimation from a sample of 45 individuals genotyped at 26 single nucleotide polymorphisms in the PIK3R1 gene. For illustration, a program embodying the method of the invention was run on a data set of 45 Caucasian individuals genotyped at 26 polymorphic SNPs in the PIK3R1 gene (phosphoinositide-3-kinase, regulatory subunit, polypeptide 1 (p85 alpha)). The distance from the first SNP to the last is about 71 kilobases. Of the 45 individuals, 1 had data missing at 1 marker and 5 had data missing at 3 markers. The genotypes were ascertained by sequencing of complete exons and of introns near intron-exon boundaries. This data was obtained using standard molecular biology techniques.

A program implementing an embodiment of this method was written in Java, version 1.2.2 and takes its input in the form of standard linkage parameter and pedigree data files, although the pointer information, sex and proband status of individuals is ignored. A skilled artisan readily recognizes that the method of the invention is not intended to be limited to such input files. The format for the input files for the implemented version of the method described in this example can be accessed on the internet at the site maintained by North Shore LIJ Research Institute or at rockefeller.edu genetic analysis software website. The current implementation accepts only markers coded as Linkage loci, however, as all codominant markers, including SNPs, can be coded this way, this is not a restriction. The program combines markers one at a time in the order listed in the input file which will usually correspond to chromosomal order. At each stage unnecessary haplotypes are eliminated and finally run 2000 EM or gene counting iterations.

Table 6 gives the MLEs for the haplotypes with estimated frequency of greater than 1%. In all, there were 343 haplotypes that had to be considered in the final gene counting. The complete analysis took under 2 seconds of CPU on a SUN Blade 1000 workstation with two 750 Mhz processors, although the program made use of only 1 processor. There is a common wild type haplotype in this population and for several markers only a single individual had the non wild-type allele.

TABLE 6

Haplotype & Frequency MLE %

| SEQ ID NO: 3 | CCAGGCTGATAATATCCAGTAAGGCA | 38.027 |
|---|---|---|
| SEQ ID NO: 4 | CCAAGCTGATAATATCCAGTAAGGCA | 8.003 |
| SEQ ID NO: 5 | CCAGACTGATAATATCCAGTAAGGCA | 5.895 |
| SEQ ID NO: 6 | CCAGGCTGATAATATCCAGTAAGGCG | 5.851 |
| SEQ ID NO: 7 | CTCGGCTGATAATATCCAGTAAGGCA | 5.059 |
| SEQ ID NO: 8 | CTCAGCTGATAATATCCAGTAAGTCA | 4.300 |
| SEQ ID NO: 9 | CTCAGCTGATAATATCCAGTAAAGCA | 2.807 |
| SEQ ID NO: 10 | CTCGGCTGATAATATCCAGTAAAGCA | 1.506 |
| SEQ ID NO: 11 | CTCGACTGATAATATCCAGTAAGGCA | 1.437 |
| SEQ ID NO: 12 | CTCGGCTGATAATACCCAGTAAGGCG | 1.111 |
| SEQ ID NO: 13 | CTCAGCTGATAATATCCAGTAAGGCG | 1.111 |
| SEQ ID NO: 14 | CTCAGCTGATAATATCCAGTAAATCG | 1.111 |
| SEQ ID NO: 15 | CTCAGCTGATAATATCCAGGAAGGCG | 1.111 |
| SEQ ID NO: 16 | CTCAGCTGACAATATCCAGTAAGGCA | 1.111 |
| SEQ ID NO: 17 | CTCAACTGATAATATCCAGTAGGGCA | 1.111 |
| SEQ ID NO: 18 | CCAGGTTGATAATATCCAGTAAGGCG | 1.111 |
| SEQ ID NO: 19 | CCAGGCTGATGATATCCAGTAAGGCG | 1.111 |
| SEQ ID NO: 20 | CCAGGCTGATAATATCTAGTAAGGCA | 1.111 |
| SEQ ID NO: 21 | CCAGGCTGATAATATCCAATAAGGCG | 1.111 |
| SEQ ID NO: 22 | CCAGGCGGATAATATCCAGTAAGGCG | 1.111 |

TABLE 6-continued

| Haplotype & Frequency MLE % | | |
|---|---|---|
| SEQ ID NO: 23 | CCAGACTGATAATGTCCAGTAAGGCA | 1.111 |
| SEQ ID NO: 24 | CCAGACTGATAATATCCAGTAAGGTG | 1.111 |
| SEQ ID NO: 25 | CCAAGCTGATAATATCCAGTGAGGCA | 1.111 |
| SEQ ID NO: 26 | CCAAGCTGATAACATCCAGTAAGTCA | 1.111 |
| SEQ ID NO: 27 | CCAAACTGATAATATCCAGTAAGTTA | 1.111 |
| SEQ ID NO: 28 | CCAAACTGATAATATCCAGTAAGGTA | 1.111 |

The method presented by the invention inherits all the features that make EM attractive for this problem. For example, the haplotype pairs that best match a given genotype set can be found, and from the weight that was allocated to that pair there is a measure of confidence in that reconstruction.

Also, the method of the invention allows for missing data, such as drop outs from the genotyping process, by allowing any pair of alleles present in the sample to match the missing observation. This, however, does have the drawback of greatly decreasing the number of haplotypes that can be eliminated if the amount of missing data is large. Moderate amounts of missing data, as in the example above are not a problem. In this example the SNPs are all in the same gene, there is strong disequilibrium between the markers, and the quality of genotyping is high with the level of missing data low. This sort of data is ideal for this computational method and it has been used in datasets with far more individuals and over 100 markers. The data used here is typical of that used in fine mapping.

As the number and density of genetic markers, especially SNPs, grows so does the potential for fine mapping of genetic traits provided we can handle this increase in information. The method presented here greatly increases the tractability of such datasets although it is not limited to such datasets.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A method for estimating the frequency of haplotypes and inferring haplotypes from genotypes for a set of individuals that comprises:
   (A) providing a set of genotypes obtained from at least two individuals comprising three or more polymorphic markers;
   (B) combining two or more markers, one or more markers and one or more loci, or two or more loci from the set of genotypes to give a new locus;
   (C) removing any haplotypes from the new locus that have a sufficiently low Maximum Likelihood Estimate (MLE) after at least one iteration of Expectation Maximum (EM) on the new locus;
   (D) repeating from step (B) one or more times, adding one or more loci or markers, until all the genotypes have been combined into a final locus;
   (F) running EM to convergence on the final locus to give the estimated frequency of haplotypes and inferred haplotypes from the set of genotypes; and
   (G) outputting the estimated frequency of haplotypes and inferred haplotypes.

2. The method of claim 1 wherein step (B) combines two markers.

3. The method of claim 1 wherein step (B) combines a marker and a locus.

4. The method of claim 1 wherein said polymorphic markers are combined one at a time.

5. The method of claim 1 wherein said polymorphic markers are combined one at a time in the order in which they appear on the chromosome.

6. The method of claim 1 wherein said sufficiently low MLE is selected from the group consisting of zero, approximately zero, approaches zero as more data is considered, or 10% of the frequency of occurrence of a particular haplotype in a dataset having k samples.

7. The method of claim 1 further comprising considering empirically derived haplotypes, haplotypes of relatives, haplotypes of family members, and degree of relatedness.

8. The method of claim 1 wherein said polymorphic markers are single nucleotide polymorphism markers (SNPs).

9. The method of claim 1 wherein said method is encoded in a machine readable form as a computer program.

* * * * *